(12) United States Patent
Luo et al.

(10) Patent No.: US 10,765,548 B2
(45) Date of Patent: Sep. 8, 2020

(54) KNEE JOINT ORTHOSIS (71) Applicant: Yun Luo, Shanghai (CN)

(72) Inventors: Yun Luo, Shanghai (CN); Yun Gan, Shanghai (CN)

(73) Assignee: Yun Luo, Shanghai (CN)

( * ) Notice: Subject to any disclaimer, the term of this patent is extended or adjusted under 35 U.S.C. 154(b) by 795 days.

(21) Appl. No.: 15/324,727

(22) PCT Filed: Jul. 7, 2015

(86) PCT No.: PCT/CN2015/083465
§ 371 (c)(1),
(2) Date: Jan. 8, 2017

(87) PCT Pub. No.: WO2016/004855
PCT Pub. Date: Jan. 14, 2016

(65) Prior Publication Data
US 2017/0196721 A1 Jul. 13, 2017

(30) Foreign Application Priority Data
Jul. 7, 2014 (CN) .......................... 2014 1 0320993

(51) Int. Cl.
A61F 5/00 (2006.01)
A61F 5/01 (2006.01)

(52) U.S. Cl.
CPC .... *A61F 5/0123* (2013.01); *A61F 2005/0134* (2013.01); *A61F 2005/0167* (2013.01)

(58) Field of Classification Search
CPC ............ A61F 5/0123; A61F 2005/0132; A61F 2005/0134; A61F 5/0102; A61F 5/01;
(Continued)

(56) References Cited

U.S. PATENT DOCUMENTS 5,092,320 A * 3/1992 Maurer ................ A61F 5/0123
602/26
5,766,140 A 6/1998 Tillinghast, III et al.
(Continued)

FOREIGN PATENT DOCUMENTS

CN 101917942 A 12/2010
CN 101938960 A 1/2011
(Continued)

*Primary Examiner* — Victoria J Hicks
(74) *Attorney, Agent, or Firm* — Im IP Law; Chai Im; C. Andrew Im (57) ABSTRACT

A knee joint protecting device includes a thigh frame connected to a shank frame by a connection structure, which includes an adjustment mechanism and a connection hinge. The thigh frame is rotatable around a first axis using the adjustment mechanism to perform a first rotation about the shank frame within a first position and a second position. When the thigh frame is in the first position, the knee joint protecting device is fit for the lower limb of a standing posture. The thigh frame performs a second rotation about the shank frame using the connection hinge, the included angle of the first axis and the rotation plane of the second rotation is within the range of 0~15°. By the adjustment mechanism and the connection hinge, the knee protecting device can provide the internal and external rotations between the thigh and the shank, and is more suitable for human engineering and kinesiology.

18 Claims, 9 Drawing Sheets

(58) Field of Classification Search
CPC ...... A61F 2005/0137; A61F 2005/0146; A61F 2005/0144; A61F 5/0125; A61F 5/013
USPC .......................................... 602/16, 26; 601/5
See application file for complete search history.

(56) References Cited

U.S. PATENT DOCUMENTS

| | | | |
|---|---|---|---|
| 6,656,144 B1 | 12/2003 | Coligado | |
| 8,060,945 B2* | 11/2011 | Adarraga | A61F 5/0102 2/22 |
| 8,747,339 B2 | 6/2014 | Schilling et al. | |
| 8,858,479 B2* | 10/2014 | Chang | A61F 5/0123 602/16 |
| 2005/0159691 A1* | 7/2005 | Turrini | A61F 5/0123 602/16 |
| 2007/0244419 A1* | 10/2007 | Mason | A61F 5/0123 602/16 |
| 2008/0195013 A1* | 8/2008 | Ingimundarson | A61F 5/0123 602/26 |
| 2010/0324462 A1 | 12/2010 | Pellis | |
| 2012/0271211 A1* | 10/2012 | Bledsoe | A61F 5/0123 602/16 |
| 2013/0035623 A1* | 2/2013 | Nace | A61F 5/0123 602/16 |
| 2014/0024987 A1* | 1/2014 | Anglada | A61F 5/0118 602/16 |
| 2014/0330187 A1* | 11/2014 | Perez | A61F 5/028 602/19 |

FOREIGN PATENT DOCUMENTS

| | | |
|---|---|---|
| CN | 202060926 U | 12/2011 |
| CN | 202161443 U | 3/2012 |
| CN | 103582468 A | 2/2014 |
| CN | 204072404 U | 1/2015 |
| FR | 2350091 A1 | 1/1978 |
| WO | 2008/129096 A1 | 10/2008 |
| WO | 2013/040354 A1 | 3/2013 |
| WO | 2013/040375 A1 | 3/2013 |
| WO | 2015/018340 A1 | 2/2015 |

* cited by examiner

KNEE JOINT ORTHOSIS

RELATED APPLICATIONS

This application is a § 371 application from PCT/CN2015/083465 filed Jul. 7, 2015, which claims priority from Chinese Patent Application No. 201410320993.0 filed Jul. 7, 2014, each of which is incorporated herein by reference in its entirety.

FIELD OF THE INVENTION

The present invention relates to a joint protecting device, especially relates to a knee joint protecting device.

BACKGROUND OF THE INVENTION

Lower limb is the lower part of human body, comprising hip, thigh, knee joint, shank and foot. The lower limb performs a function of supporting the human body while standing or walking and enables the human body to be in many kinds of postures such as sitting, kneel sitting and prone. The main parts of the human body for supporting the weight of the body are bones of lower limbs, namely lower limb bones, which include the bone of lower limb girdle and the bones of free lower limbs. The bone of lower limb girdle is the innominate bone, and the bones of free lower limbs include femur, patella, tibia, fibula, seven tarsal bones, five metatarsal bones and fourteen toe bones. A connection part of bones is called a joint, and there are three main joints in the lower limb: hip joint, knee joint and ankle joint. All of the three joints are weight-bearing joints.

The bones or joints of lower limb in a human body may suffer lesion or degeneration because of aging, diseases and accidents. The lesion or degeneration of lower limb joints may affect their weight-bearing function, and may further affect standing, walking, running and jumping of human body. In this situation, drug therapy, traditional physical therapy and rehabilitation therapy are always applied, and in serious situation operative treatment is applied to recover the function of lower limb bones or joints as well. In a rehabilitation therapy, an orthosis is always used.

Orthosis, also known as brace, is an in-vitro device used at human limbs or other locations to prevent and correct deformity, cure diseases of bones, joints and nervus, and compensate their functions. The orthosis can relieve the dysfunction of limbs, spine and musculoskeletal system by restricting or assisting body movement or by changing the force line of human body. According to different application locations, the orthosis can be divided into three classes: upper limb orthosis, spinal orthosis and lower limb orthosis. In the three kinds of orthosis, the upper limb orthosis is mainly used to compensate the loss of muscle strength, support the paralytic body, keep and hold limbs or postures, supply traction to prevent contracture and prevent or correct deformity; the spinal orthosis is mainly used to relieve regional pain, protect diseased region from further injury, support the paralytic body and prevent or correct deformity; the lower limb orthosis is used to fix the diseased joints, prevent or correct deformity, compensate for the loss of muscle strength, improve the gait, prevent limbs from bearing weight, promote fracture healing and function recovery.

Figure 1:
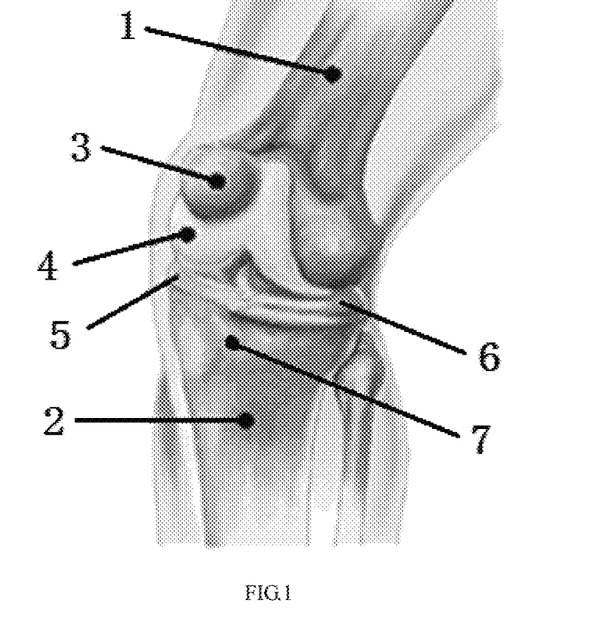
FIG. 1 is a structure illustration of the anatomical structure of a knee joint in human body.

The knee joint is one of the significant weight-bearing joints in lower limbs. As shown in FIG. 1, the knee joint connects femur 1 in the thigh and tibia 2 in the shank, comprising an articular cartilage 4, a medial meniscus 5 and a lateral meniscus 6. According to kinesiology analysis, there are many kinds of movement in the knee joint when the lower limb changes from a bend status to a straight status. For example, when the shank wiggles, the bend angle of passive bend is 0~140°; meanwhile the thigh can rotate an angle around the long axis of the shank, which is called internal rotation and external rotation, and the angle is about 30° in the situation of initiative rotation.

Figure 2:
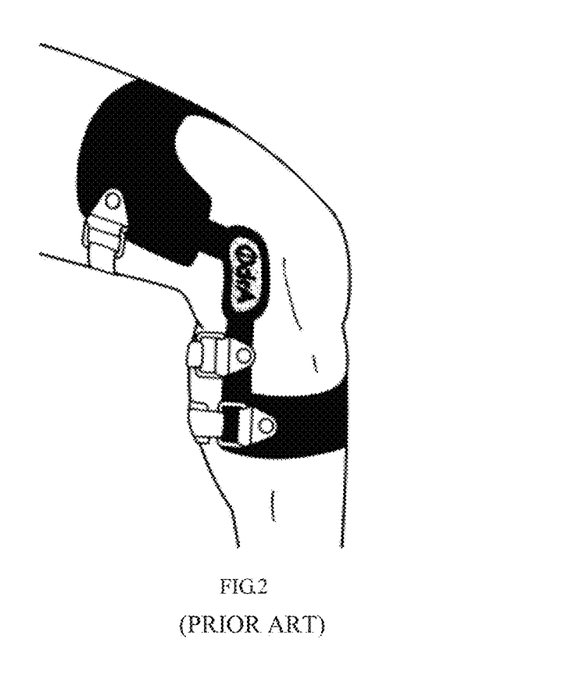
FIG. 2 shows Odra's orthosis.

The inner structure of knee joint may be damaged by the reason of external force impact or degeneration and diseases such as ligamentous injury, cartilaginous degeneration and meniscus wear, and knee pain and dyskinesia may further occur. To solve the above-mentioned problems, knee joint assistive devices are designed for different diseases or injuries. For example, PCL and ACL assistive devices designed for cruciate ligament injury, and nonbearing assistive devices (orthosis) designed for knee osteoarthritis. So far, most of knee joint assistive devices (orthosis) comprise two lateral hinges, whose rotation planes are parallel, to connect thigh frame and shank frame without considering the internal rotation and external rotation between the thigh and the shank, so such assistive devices can only perform a rotation along the rotation planes of lateral hinges. When patients wear such assistive devices, their movement of the internal rotation and external rotation between thigh and shank will be restricted, and the force balance in the knee joint will be changed. Odra from France has designed an assistive device which can perform a proactive internal rotation (seen on the website www.odra.ca/en/) shown in FIG. 2. However, the angle of internal rotation is constant, which is not fit for everybody, and the space between the lateral hinge and the knee joint is so large that low fitness and poor appearance are caused, which affects the acceptability of users.

Moreover, most assistive devices need to put a force from the front direction on the shank so as to fix the shank, so these devices comprise a shank bracket with soft belts or curved rigid structure to press the shank. Since the tibia will bear a large pressure, and the soft tissue layer of the front position of the shank is too thin that the position is sensitive to pressure, the existing assistive devices are poor in comfort.

Therefore, technical personnel are working at developing a knee joint protecting device, which can fit for the movement of knee joint and increase the comfort of shank in wearing.

SUMMARY OF THE INVENTION

In consideration of such defects of above-mentioned prior art, the technical problem which the present invention aiming at is to provide a knee protecting device, which can increase the comfort of shank in wearing by means of setting a kind of connection structure with two degrees of freedom to fit the movement of knee joint.

To achieve the above-mentioned purpose, the present invention provide a knee joint protecting device, comprising a thigh frame used to be worn on the thigh of a lower limb and a shank frame used to be worn on the shank of said lower limb, said thigh frame is connected to said shank frame and can perform a rotation around a first axis, which passes the connecting position of the two, about said shank frame within a first position and a second position; when said thigh frame is at said first position, said knee joint protecting device is fit for said lower limb of a standing posture, wherein said thigh frame can perform a second rotation about said shank frame, the included angle of said first axis and the rotation plane of said second rotation is within the range of 0~15°.

Furthermore, the knee joint protecting device comprises: a connection structure set between said thigh frame and said shank frame, said connection structure comprising an adjustment mechanism and a connection hinge, which are connected with each other, said thigh frame perform said rotation by said adjustment mechanism, said thigh frame perform said second rotation by said connection hinge, said connection position is on said adjustment mechanism.

Furthermore, said adjustment mechanism comprises a groove plate and a sliding block, which can rotate about each other, one of said groove plate and said sliding block is connected to said thigh frame by said connection hinge, and the other one is fixed on said shank frame.

Furthermore, said thigh frame comprises two thigh splints used to fit said thigh, said knee joint protecting device comprises two said connection structures, said connection hinges of said two connection structures are connected with said two thigh splint respectively, said connection hinge comprises a first hinge part and a second hinge part, which can rotate about each other, said first hinge part is fixed on said thigh frame, said second hinge part is connected with said adjustment mechanism, when said thigh frame is at said first position, the included angle of said first axis and the rotation axis of said first hinge parts of said two connection hinges is 90°±30°, and preferably 90°±20°.

Furthermore, one of said two thigh splints is a first thigh splint used to fit on the inner side of said thigh and the other one is a second thigh splint used to fit on the outer side of said thigh frame, said two connection structures are used to fit on two sides of the knee joint respectively.

Furthermore, said second hinge part is fixed on said adjustment mechanism, for one said thigh splint and the attached connection hinge and the attached adjustment structure, the rotation plane where said groove plate and said sliding block rotate about each other is a first rotation plane, and the rotation plane where said first hinge part and said second hinge part rotate about each other is a second rotation plane, when said thigh frame is at said first position, the included angle of said first rotation plane and said second rotation plane is 90°±25°, and preferably 90°±10.

Furthermore, said second hinge part is connected to said adjustment mechanism by a rivet or a screw.

Furthermore, said second hinge part is rotatably connected with said adjustment mechanism, for one said thigh splint and the attached connection hinge and the attached adjustment structure, the rotation plane where said groove plate and said sliding block rotate about each other is a first rotation plane, and the rotation plane where said second hinge part and said adjustment mechanism rotate about each other is a third rotation plane, when said thigh frame is at said first position, the included angle of said second rotation plane and said third rotation plane is 90°±40°, and preferably 90°±30.

Furthermore, said second hinge part is connected to said adjustment mechanism by a hinge pin, the relative rotation of said second hinge part and said adjustment mechanism is performed around said hinge pin.

Furthermore, said thigh frame performs a stretch outward when said thigh frame turns to said second position from said first position, said thigh frame performs a shrink inward when said thigh frame turns to said first position from said second position, said thigh frame performs said stretch and said shrink by said connection hinge.

Furthermore, the rotation plane where said groove plate and said sliding block rotate about each other is a first rotation plane, said connection hinge comprises a first hinge part and a second hinge part, which can rotate about each other, the rotation plane where said first hinge part and said second hinge part rotate about each other is a second rotation plane, said second hinge part is rotatably connected to said adjustment mechanism, and the rotation plane where said second hinge part and said adjustment mechanism rotate about each other is a third rotation plane, when said thigh frame is at said first position, the included angle of said second rotation plane and said third rotation plane is 90°±40°, and preferably 90°±30.

Furthermore, the included angle of said first axis and said first rotation plane is 55°~75°.

Furthermore, said thigh frame comprises two thigh splints used to fit said thigh, said knee joint protecting device comprises two said connection structures, said first hinge parts of said connection hinge of said two connection structures are fixed on said thigh frame respectively, when said thigh frame is at said first position, the included angle of said first axis and the rotation axis, around which said first hinge part rotates about said second hinge part, is 90°±30°, and preferably 90°±20°.

Furthermore, one of said two thigh splints is a first thigh splint used to fit on the inner side of said thigh and the other one is a second thigh splint used to fit on the outer side of said thigh frame, said two connection structures are used to fit on two sides of the knee joint respectively, the included angle of two rotation planes where said sliding blocks rotate about said groove plates of said two adjustment mechanisms respectively is 30°~70°.

Furthermore, for one said thigh splint and the attached connection hinge and the attached adjustment structure, when said thigh frame is at said first position, the included angle of said first rotation plane and said second rotation plane is 90°±25°, and preferably 90°±10.

Furthermore, said second hinge part is connected to said adjustment mechanism by a hinge pin, the relative rotation of said second hinge part and said adjustment mechanism is performed around said hinge pin.

Furthermore, wherein said second hinge part is connected to said first hinge part by a second hinge pin, the relative rotation of said first hinge part and said first hinge part is performed around said second hinge pin, said second hinge pin is perpendicular to the contacting plane of said first hinge part and said second hinge part.

Optionally, there is a contacting plane between said first hinge part and said second hinge part, said hinge pin at least penetrates through part of said first hinge part and part of said second hinge part successively.

Optionally, there are plural contacting planes between said first hinge part and said second hinge part, said hinge pin at least penetrates through part of said first hinge part and part of said second hinge part successively.

Furthermore, one of said first hinge part and said second hinge part comprises a bulge extending along the direction perpendicular to said second rotation plane, and the other one comprises a guiding groove matching said bulge, the relative rotation is performed by means of that said guiding groove holds said bulge and allows said bulge to rotate inside.

Furthermore, said thigh frame further comprises a thigh bracket to horizontally fit the front surface of said thigh, the end portions, which are away from said shank splints, of said two thigh splints are connected with said thigh bracket, said thigh bracket is a flexible construction with a curving shape, the curve radius of said thigh bracket turns smaller when said thigh frame shrinks inward, and turns larger when said thigh frame stretches outward.

Furthermore, said thigh splint can rotate around the connecting point where said thigh splint connects with said thigh bracket.

Furthermore, a cushion pad is set on the inner surface of said thigh bracket, the surface of said cushion pad is a layer of net-shaped silicon.

Furthermore, a second adjustment mechanism is set between said first hinge part and said thigh splint, used to adjust and set the relative position of said first hinge part and said thigh splint.

Optionally, said second adjustment mechanism comprises: a first hole set on said first hinge part; a group of second holes, used to match said first hole, set on the end portion of said thigh splint; and a connecting piece, the adjustment of the relative position of said first hinge part and said thigh splint is performed by means of selecting and aligning said first hole and one of said second holes, and then penetrating them by a connecting piece to fix the first hinge part and the thigh splint firmly.

Optionally, said second adjustment mechanism comprises: a first ratchet structure set on said first hinge part; a second ratchet structure, used to match said first ratchet structure, set on the end portion of said thigh splint; and a connecting piece, the adjustment of the relative position of said first hinge part and said thigh splint is performed by means of adjusting the meshing position of said first ratchet structure and said second ratchet structure and then fixing said first hinge part to said thigh splint by said connecting piece.

Optionally, said second adjustment mechanism comprises: groove set on said first hinge part; a bulge portion, used to match said groove, set on the end portion of said thigh splint; two set screws penetrating said first hinge part from two sides until said groove respectively, the adjustment of the relative position of said first hinge part and said thigh splint is performed by means of adjusting said set screws to clamp said bulge portion in said groove.

Furthermore, said shank frame comprises a shank bracket used to fit the middle part of said shank horizontally, said shank bracket comprises a first portion and a second portion with different curvature, both end portions of said first portion and said second portion are connected respectively, the flexibility of said first portion is smaller than said second portion, said first portion is set at the outside of said second portion.

Furthermore, said end portions of said first portion and said second portion are connected by screw posts.

Furthermore, said shank frame further comprises a shank splint, shaped like a butterfly, used to fit the top part of said shank, said shank splint comprises a middle portion and four wing portions extending from said middle portion, two of said wing portions on the upper crookedly extends upward, and the two ends of them are connected with said two adjustment mechanism respectively, two of said wing portions on the bottom extends horizontally, and the two ends of them are connected with two ends of a first shank belt, said used to cross over the back surface of the shank at rhombus sunk area of the posterior region of the knee, the middle portion of said shank splint is connected with said first portion.

Furthermore, two ends of said second portion are connected with two ends of a second shank belt respectively, said second shank belt is used to cross over the calf.

Furthermore, a cushion pad is set on the inner surface of said second portion, the surface of said cushion pad is a layer of net-shaped silicon.

In one preferred embodiment, the knee protecting device comprises a thigh frame and a shank frame, wherein the thigh frame is used to be worn on the thigh, and the shank frame is used to be worn on the shank. The thigh frame is connected with the shank frame by a connection hinge and an adjustment mechanism, and the connecting position of the thigh frame and the shank frame is the adjustment mechanism. The adjustment mechanism comprises two portions, which can rotate about each other. The two portions connected with the thigh frame and the shank frame respectively to perform the relative rotation of the thigh frame and the shank frame and the rotation follows the bend and straight movement which the thigh performs about the shank. The thigh can rotate within a first position and a second position, wherein when the thigh frame is at the first position, the knee protecting device fits for the lower limb in a standing posture in which the thigh frame and the shank frame are in straight status and the included angle of the two is about 180°. When the thigh frame is at the second position, the knee protecting device fits for the lower limb in a most bend posture in which the included angle of the thigh frame and the shank frame is about 30~40°.

Two rotation planes, located on inner side and outer side respectively, of two adjustment mechanisms (the first rotation plane is the plane where one portion of the adjustment mechanism rotate about the other portion, or the plane perpendicular to the rotation axis) are not parallel to each other, and there is an included angle between them. When the knee protecting device of the present invention is worn, the relative position of the two adjustment mechanisms and the knee joint is: in the direction of up and down, the adjustment mechanisms are close to the tibial plateau; in the direction of left and right, the adjustment mechanisms are respectively on each side of the patella and close to the near-end of the tibia; in the direction of front and back, the adjustment mechanisms are at the positions of about front ⅓ part of the knee joint. Generally the rotation planes of the two adjustment mechanisms present an 30~70° included angle, and in a preferred embodiment of the present invention the included angle α (shown in FIG. 15) is 50°. Since is wide in the middle and narrow in the front and back, so the cross section of knee joint is oval-shaped. Therefore the included angle can make two adjustment mechanisms fit the lower limb better, and make the knee joint protecting device more convenient and comfortable.

In one preferred embodiment, two connection hinges are respectively connected with two thigh splints upward and respectively connected with two adjustment mechanisms downward. The connection hinge includes a first hinge part and a second hinge part, which can rotate about each other. Wherein the rotation plane where the first hinge part and the second hinge part rotate about each other is a second rotation plane. The connection hinge can be fixed on the adjustment mechanism, also can be rotatably connected with the adjustment mechanism. The thigh frame can perform a second relative rotation about the shank frame according to the relative rotation of the first hinge part and the second hinge part. The rotation plane of the second relative rotation is almost parallel to the first axis, which passes the connection position of the thigh frame and the shank frame (as axis EF shown in FIG. 15). Generally the included angle of the first axis and the rotation plane is within the range of 0~15°.

When the connection hinge is fixed to the adjustment mechanism and the thigh frame is at the first position, the included angle of the first axis and the rotation axis, around which the first hinge part rotates about the second hinge part, is preferably 90°±30°, and more preferably 90°±20°; the included angle of said first rotation plane and said second rotation plane is preferably 90°±25°, and more preferably 90°±10.

When the connection hinge is rotatably connected with the adjustment mechanism, the rotation plane where the second hinge part and the adjustment mechanism rotate about each other is a third rotation plane. In this case when the thigh frame is at the first position, the included angle of the first axis and the rotation axis, around which the first hinge part rotates about the second hinge part, is preferably 90°±30°, and more preferably 90°±20°; the included angle of the second rotation plane and the third rotation plane is preferably 90°±40°, and more preferably 90°±30; the included angle of the first rotation plane and the second rotation plane is preferably 90°±25°, and more preferably 90°±10. Such ranges of the angles mentioned above are set for fitting different shape of human bodies, such as O-shapes legs and X-shaped legs.

Such a design ensures that the thigh frame comprises enough degrees of freedom and flexibility, so that the thigh frame can perform the bend and straight movement about the shank frame, and can rotate an angle around the axis of the thigh, namely the internal rotation and the external rotation described in the background.

Moreover, the cross section shape of the thigh will change as the status changing of bend or straight. Specifically, the shape changing presents as: compared with the straight status, the cross section shape of the thigh is larger in the bend status, especially when a person is squatting, the soft tissue in the thigh is pressed and become obviously wider. So the width of the thigh frame needs to be changeable as the bend angle changes to enhance the comfort. Since the rotation planes of the two adjustment mechanisms will open backward when the bend angle increases, the distance between the connecting positions of two adjustment mechanisms and the thigh frame will increase, so the width of the thigh frame will be actuated to increase as well. So the width change of the thigh can be adapted. Specifically, the process is: when the thigh frame rotate toward the shank frame (namely, the bend angle between the thigh frame and the shank frame increases), the thigh frame stretches outward (namely, the width of the thigh frame becomes larger); when the thigh frame rotate away from the shank frame (namely, the bend angle between the thigh frame and the shank frame decreases), the thigh frame shrinks inward (namely, the width of the thigh frame becomes smaller). Therefore such a design can fit the actual movement, which includes the bend and straight movement, the internal rotation and the external rotation, of the knee in human body. On the contrary, an orthosis which only considers the bend and straight movement will restrict the movement of internal rotation and external rotation.

In one preferred embodiment, a second adjustment mechanism is set between the thigh frame and the shank frame to adjust and set the relative angle of the thigh frame and the shank frame to match different width of the thigh of different users, further to enhance the adaption of the knee joint protecting device in the present invention.

In one preferred embodiment, the shank frame comprises a shank splint, a shank bracket and shank belts. The two end portions of the shank splint are used to connect with the two adjustment mechanisms respectively, and the middle portion is used to connect with the shank bracket.

The shank bracket is composed of a rigid first portion and a flexible second portion, and presents a bow shape. The two end portions of the second portion (hereinafter referred as shank bracket bowstring) are fixed on and tensed on the first portion (hereinafter referred as shank bracket bow), and there is an interval between the shank bracket bowstring and the middle portion of the shank bracket bow. The shank bracket bowstring contacts the shank, so though the shank bracket cross over the shank, but the main weight bearing position will not be the tibia. The whole shank bracket crosses over the shank, wherein the shank bracket bowstring whose middle presses on the tibia position, contacts the shank, and the rigid part of the shank bracket bow presses on the soft tissue on each side of the tibia. So when the knee protecting device is worn on, the force that the knee protecting device applies on the shank can be shared reasonably: firstly, the main force can be borne by the shank bracket bow and the soft tissue on each side of the tibia, and further be shared equally onto the soft tissue by the shank bracket bowstring; secondly, the shank bracket bowstring is stripe shaped and the middle portion of the shank bracket bowstring presses on the shank, so the shank bracket bowstring can bear a smaller force and can avoid an overlarge force, further enhance the comfort greatly. Moreover, cushion pads are set on the inner surface of the thigh bracket and the shank bracket bowstring, so as to enhance the weight bearing function of the shank bracket and prevent the knee protecting device from sliding. The cushion pad is preferably a composite cushion with a layer of silicon drops arranged as net shape. Moreover, such cushion pads can be also set on the upper portion of the shank splint, so as to ensure that the shank splint will not hurt the shank under impact.

The embodiment of the present invention will be described in detail herein below with reference to the figures for explaining the art solution, features, purpose and effects of the present invention.

DETAILED DESCRIPTION OF THE INVENTION

Embodiment

Figure 3:
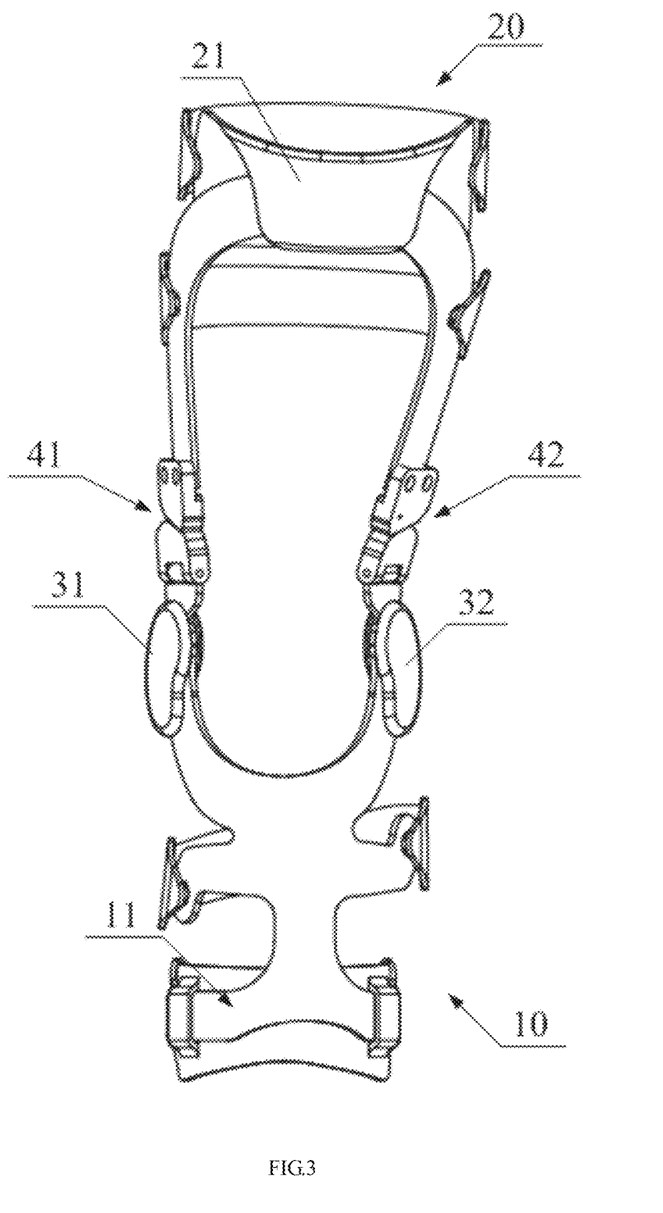
FIG. 3 is a front view of a preferred embodiment of the knee protecting device in the present invention.
Figure 4:
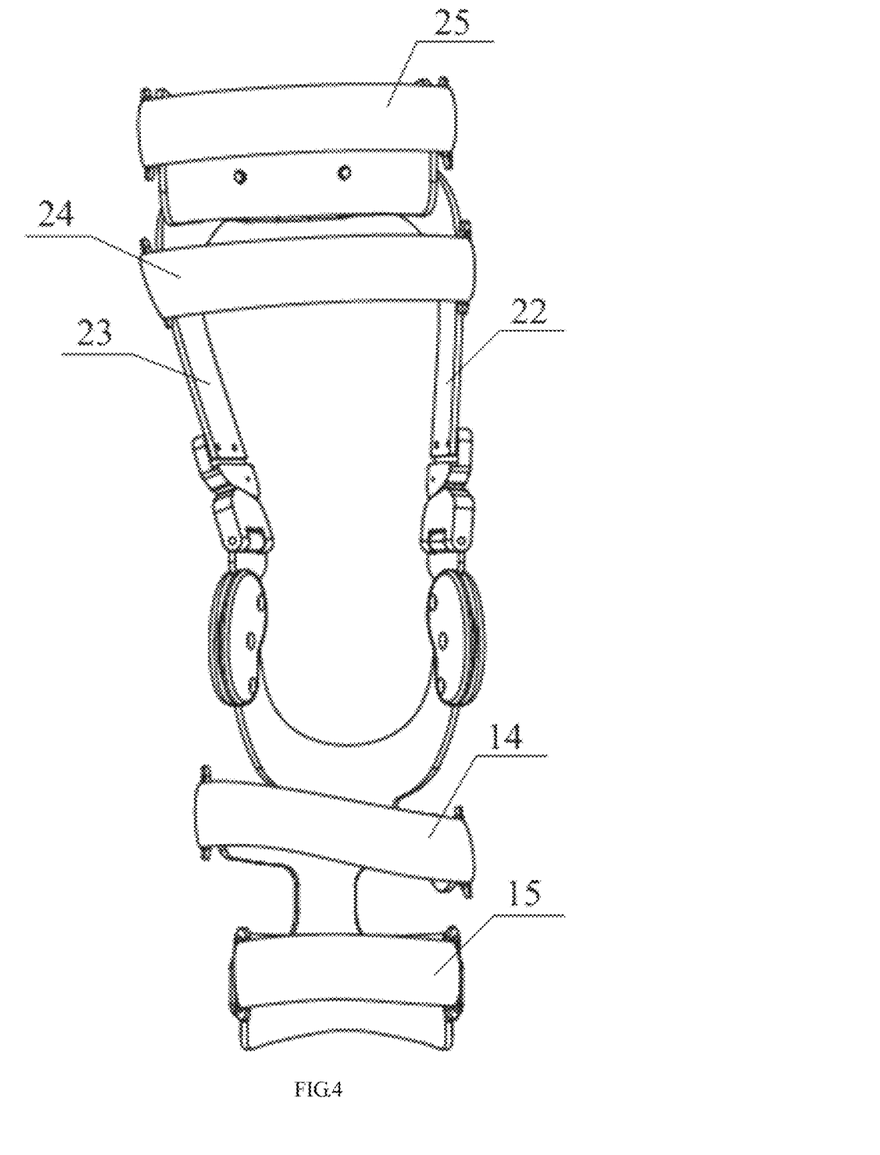
FIG. 4 is a back view of the knee protecting device shown in FIG. 3.
Figure 5:
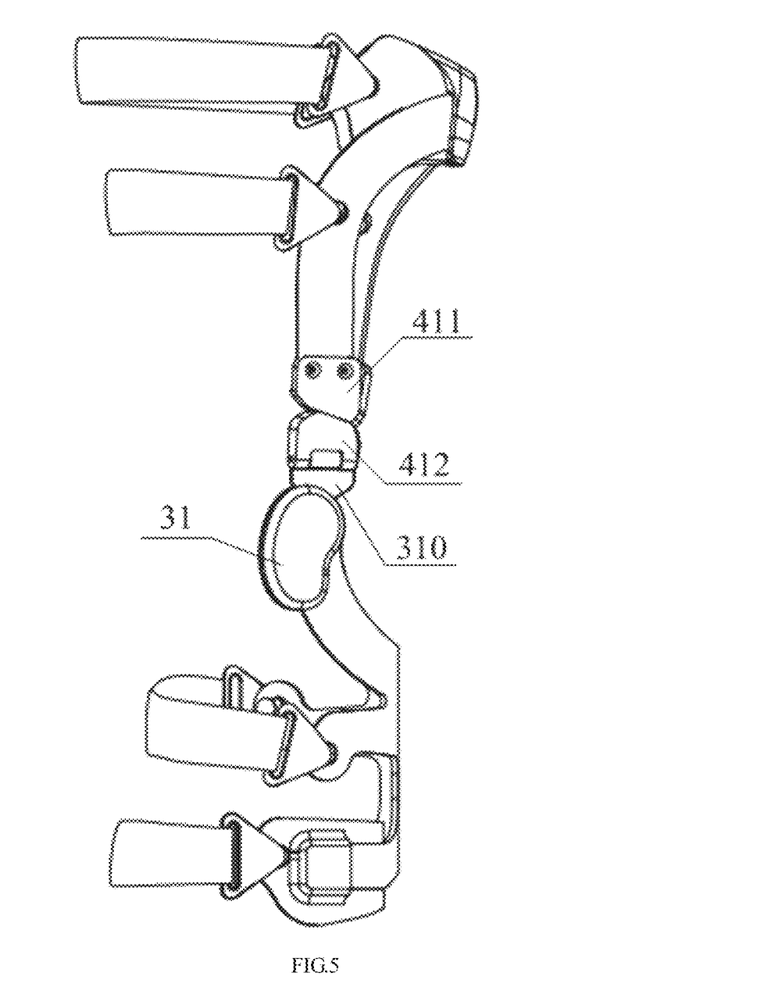
FIG. 5 is a side view of the knee protecting device shown in FIG. 3.

As shown in FIGS. 3-5, the knee joint protecting device of the present invention comprises a thigh frame 20 and a shank frame 10. The thigh frame 20 is used to be worn on the thigh, and the shank frame 10 is used to be worn on the shank. Wherein the thigh frame 20 comprises a thigh bracket 21, two thigh splints 22, 23 and two thigh belts 24, 25; the shank frame 10 comprises a shank bracket 11, a shank splint 16 (shown in FIG. 12) and two shank belts 14, 15. The thigh splint 22 is connected with the shank splint 16 by a connection hinge 41 and an adjustment mechanism 31, and the thigh splint 23 is connected with the shank splint 16 by a connection hinge 42 and an adjustment mechanism 32. Thus the connection hinge 41 and the adjustment mechanism 31 compose one connection structure between the thigh frame 20 and the shank frame 10.

The working status of the knee joint protecting device of the present invention is divided into a first status and a second status. As the user who wears the knee joint protecting device of the present invention moves the lower limb from the bend status to the straight status, the adjustment mechanism makes the knee joint protecting device to change the working status from the second status to the first status. When the knee joint protecting device is in the first status, the thigh frame binds the thigh tightly, the shank frame binds the shank tightly, the thigh frame performs a force on the thigh along the mechanical axis of the femur and against the shank, and the shank frame performs a force on the shank along the mechanical axis of the tibia and against the thigh. As the user who wears the knee joint protecting device of the present invention moves the lower limb from the bend status to the straight status, the adjustment mechanism makes the knee joint protecting device to change the working status from the first status to the second status. When the knee joint protecting device is in the second status, the thigh frame unbinds the thigh tightly, the shank frame unbinds the shank tightly, the thigh frame releases the force on the thigh along the mechanical axis of the femur and against the shank, and the shank frame releases the force on the shank along the mechanical axis of the tibia and against the thigh. Such working statuses are the same as the knee orthosis described in Chinese patent A nonbearing knee orthosis (application No. CN201310347765.8), and the present invention references the above description of the Chinese patent A nonbearing knee orthosis (application No. CN201310347765.8).

The adjustment mechanism is the same as the adjustment mechanism in the Chinese patent A nonbearing knee orthosis (application No. CN201310347765.8), including a groove plate and a sliding block. The present invention references the description about the adjustment mechanism in the Chinese patent A nonbearing knee orthosis (application No. CN201310347765.8). For example, in the adjustment mechanism 31 the groove plate and the shank splint are fixed together (same as the fixed connection of the groove plate and the shank splint in the Chinese patent A nonbearing knee orthosis, application No. CN201310347765.8, so the detail is no more described here), and the sliding block 310 is connected to the thigh splint 22 by the connection hinge 41.

Figure 15:
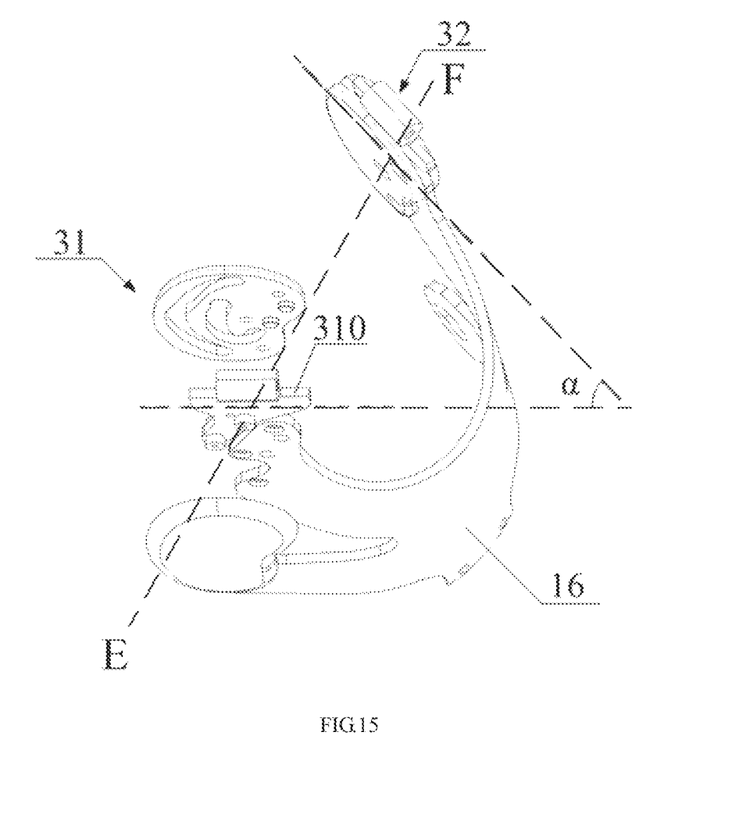
FIG. 15 shows the adjustment mechanism and the connection way of the mechanism and the shank splint of the knee protecting device shown in FIG. 3.

In the present invention, the rotation planes of the adjustment mechanisms 31 and 32 (the plane where the sliding block and the groove plate rotate relatively, or the plane perpendicular to the rotation axis of the sliding block and the groove plate; and in the present embodiment the rotation plane is the contact surface of the sliding block and the groove plate) are not parallel with each other, and there is a forward included angle between the two planes. As shown in FIG. 15, the angle α of the rotation planes of the adjustment mechanisms 31 and 32 is preferably an angle of 30~70°, and more preferably 50°.

Figure 6:
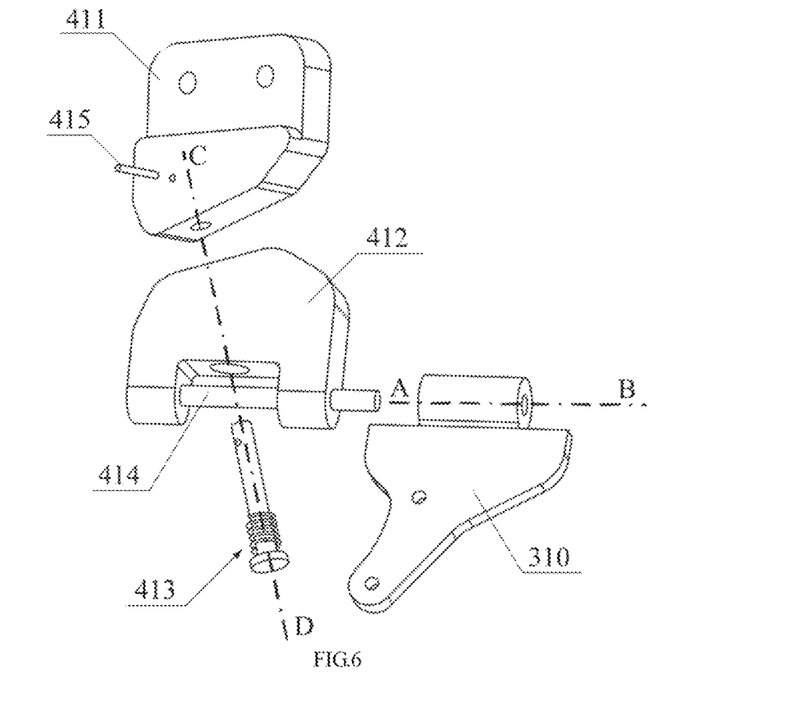
FIG. 6 shows one structure of the connection hinge of the knee protecting device shown in FIG. 3.

FIG. 6 shows one structure of the connection hinge and its connection way with the sliding block in the adjustment mechanism. As shown in FIG. 6, the connection hinge 41 includes a first hinge part 411 and a second hinge part 412. The first hinge part 411 is used to connect with the end portion of the thigh splint 22, and they can be fixed by screws, etc. A through-hole is set on the end portion of the sliding block 310, covering a hinge pin 414 which is set on the second hinge part 412. Holes fit for the hinge pin 413 are respectively set in the first hinge part 411 and the second hinge part 412, and a hole fit for pin 415 is set in the first hinge part 411. A protruding flange is set at one end of the hinge pin 413, on which a spring is set. A hole fit for pin 415 is set on the other end of the hinge pin 413. As the hinge pin 413 penetrates through the second hinge part 412 and the first hinge part 41 successively, and the pin 415 penetrates through the first hinge part 41 and the hinge pin 413 successively, the connection hinge 41 is assembled. The connection hinge 41 possesses two degrees of freedom: it can rotate around the axis AB about the sliding block 310, in other words, the rotation plane about the sliding block 310 is the plane which passes the contacting point of two and is perpendicular to the axis AB; wherein the first hinge part 411 and the second hinge part 412 can rotate about each other around the axis CD, in other words, the rotation plane of the first hinge part 411 and the second hinge part 412 is the plane which passes the contacting point of two and is perpendicular to the axis CD.

Figure 7:
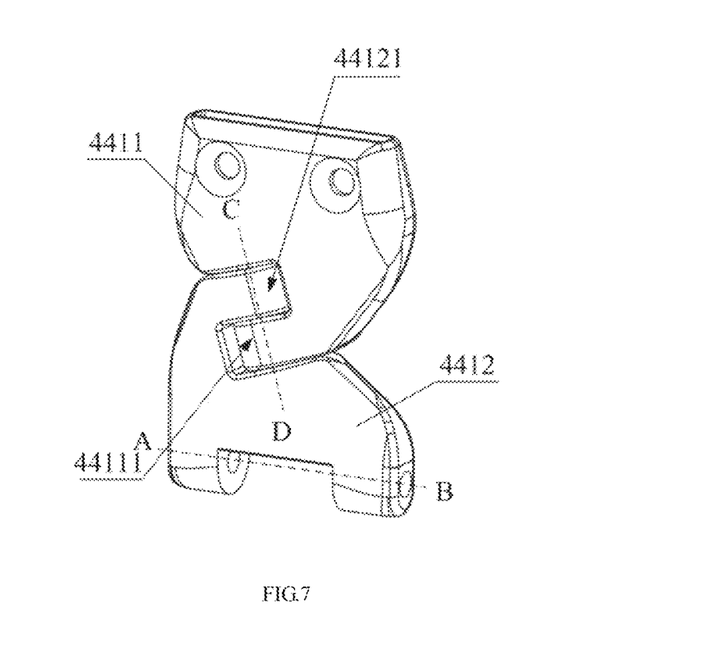
FIG. 7 shows another structure of the connection hinge.

FIG. 7 shows another structure of the connection hinge. Compared with the previous structure, in this structure the first hinge part 4411 and the second hinge part 4412 are also connected by a hinge pin (not shown in the figure) which extends along the axis CD, and the second hinge part 4412 is also connected to the adjustment mechanism by a hinge pin which extends along the axis AB, and the detail is no more described here below. The different point is that, in this structure, the first hinge part 4411 and the second hinge part 4412 possess more than one contacting surfaces which are parallel with the rotation planes of the two respectively. As shown in FIG. 7, there're three contacting surfaces as described above. That is, the first hinge part 4411 and the second hinge part 4412 both have some parts embedded in each other, and also both have some other parts contacting each other. For example, the first hinge part 4411 possesses a bulge portion 44111, and the second hinge part 4412 possesses a bulge portion 44121; the first hinge part 4411 possesses a groove for fitting the bulge portion 44121, and the second hinge part 4412 possesses a groove for fitting the bulge portion 44111. After the grooves and the bulge portions are meshed together, the first hinge part 4411 and the second hinge part 4412 can be assembled together, and then the hinge pin along the axis CD can penetrate part of the first hinge part 4411, part of the second hinge part 4412, part of the first hinge part 4411 and part of the second hinge part 4412 successively. It can be seen that, compared with the previous structure wherein there is only one contacting surface between the first hinge part 411 and the second hinge part 412, in this structure the part of the hinge pin to bear the force along the axis direction is longer, and there are plural force bearing points whereon, so this structure performs better on bent-resistant, further makes that the connection hinge is assembled well and not easy to be disengaged.

Figure 8:
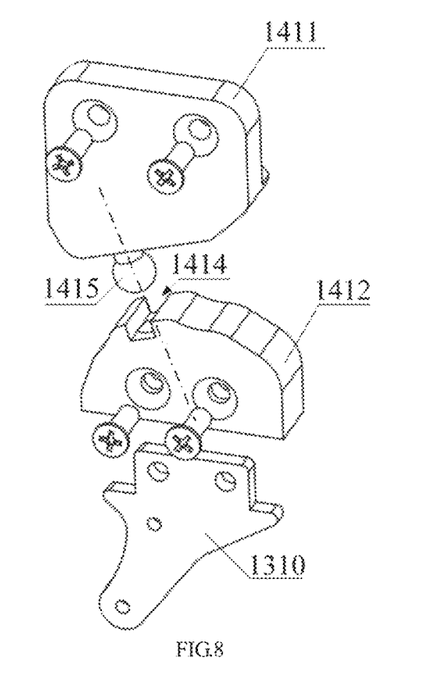
FIG. 8 shows another more structure of the connection hinge.

FIG. 8 shows another structure of the connection hinge and its different connection way with the sliding block of the adjustment mechanism. As shown in FIG. 8, the connection hinge 141 includes a first hinge part 1411 and a second hinge part 1412. The first hinge part 1411 is used to connect with the end of the thigh splint 22, and they can be fixed by screws (the screws for fixation are shown in the figure). The second hinge part 1412 is used to connect with the end portion of a sliding block 1310, and they can be fixed by screws (the screws for fixation are shown in the figure). The end portion of the first hinge part 1411 and the second hinge part 1412 are connected by a spherical hinge. The first hinge part 1411 possesses a bulge 1415, which includes a spherical portion and a stick portion; the second hinge part 1412 comprises a guiding groove 1414. A spherical cavity is set on the bottom of the guiding groove 1414 for fitting the spherical portion of the bulge 1415, and the spherical cavity includes an open on the bottom surface of the guiding groove 1414. So that the spherical portion of the bulge 1415 can be engaged in the spherical cavity, and the stick portion can be limited in the guiding groove 1414. The first hinge part 1411 and the second hinge part 1412 can rotate about each other in two directions: rotate around the axis direction of the stick portion of the bulge 1415, namely, the rotation plane of first hinge part 1411 about the second hinge part 1412 is the plane which passes the contacting point of the two and is perpendicular to the axis of the stick portion; and rotate within the rotation plane which passes the center point of the spherical portion and is parallel with the extending direction of the guiding groove 1414, namely, the rotation plane of first hinge part 1411 about the second hinge part 1412 is the plane which passes the contacting point of the two and is parallel to the extending direction of the guiding groove 1414.

Figure 9:
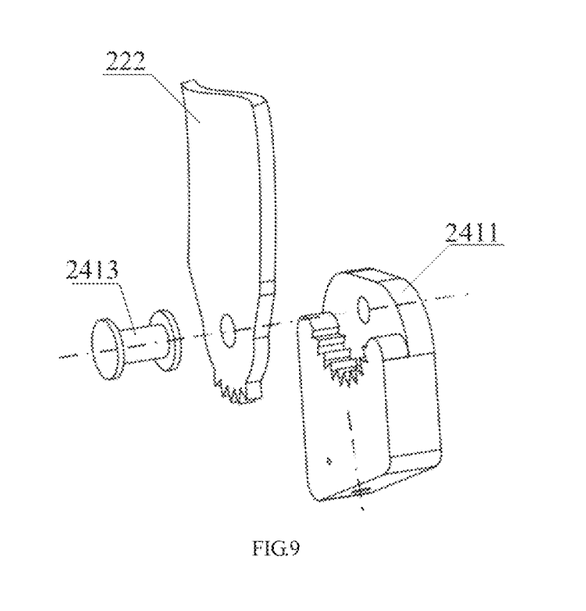
FIG. 9 shows one connection way of the connection hinge and the thigh splint, which can adjust the included angle of the first hinge part and the thigh splint discretely.

Despite the above mentioned connection way of the first hinge part and the end portion of the thigh splint, a second adjustment mechanism can be also set between the first hinge part and the thigh splint to adjust the relative position of the first hinge part and the thigh splint. In other words, the connection between the first hinge part and the thigh splint can be a rotatable connection for adjusting the relative position (included angle) between the first hinge part and the thigh splint so as to meet needs of different users. FIG. 9 shows a structure which can adjust the included angle of the first hinge part and the thigh splint discretely, and FIG. 10 shows a structure which can adjust the included angle of the first hinge part and the thigh splint steplessly.

As shown in FIG. 9, the first hinge part 2411 and the end portion of the thigh splint 222 are connected by a screw posts 2413, and the first hinge part 2411 and the end portion of the thigh splint 222 respectively possess a ratchet structure matching with each other. When adjusting the relative position of the two, the screw posts 2413 need to be loosened firstly, and then the ratchet structures are adjusted until the included angle is proper, at last the crew posts 2413 can be tightened to fix the first hinge part 2411 and the thigh splint 222 firmly.

Figure 10:
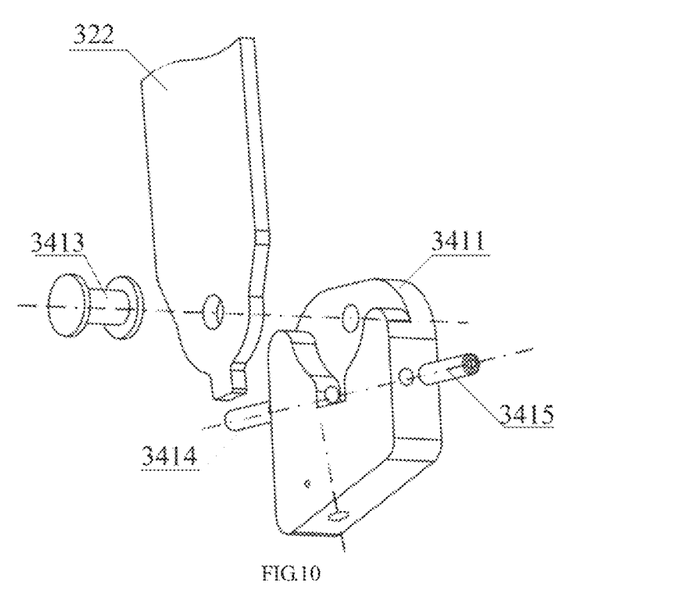
FIG. 10 shows another connection way of the connection hinge and the thigh splint, which can adjust the included angle of the first hinge part and the thigh splint steplessly.

As shown in FIG. 10, the first hinge part 3411 and the end portion of the thigh splint 322 are connected by screw posts 3413, and they can rotate about each other. A bulge portion is set on the end portion of the thigh splint 322, and a groove wider than the bulge portion is set on the first hinge part 3411. The bulge portion is engaged into the groove, and there are set screws 3414, 3415 on two sides of the groove respectively. The set screws 3414, 3415 hold and clamp the bulge from two sides. When adjusting the relative position of the first hinge part 3411 and the thigh splint 322, the set screws 3414, 3415 can be screwed to control the movement of the bulge portion of the thigh splint 322 to rotate about the first hinge part 3411 until required position.

Moreover, the second adjustment mechanism can be performed by means of connecting piece and corresponding connecting hole. For example, a first hole set on the first hinge part and a group of second holes corresponding to the first hole respectively can be used, so that the first hole and one second hole can be selected to be aligned and penetrated by a connecting piece to fix the first hinge part and the thigh splint firmly. Therefore different selections can perform the adjustment of the relative position of the first hinge part and the thigh splint.

Figure 11:
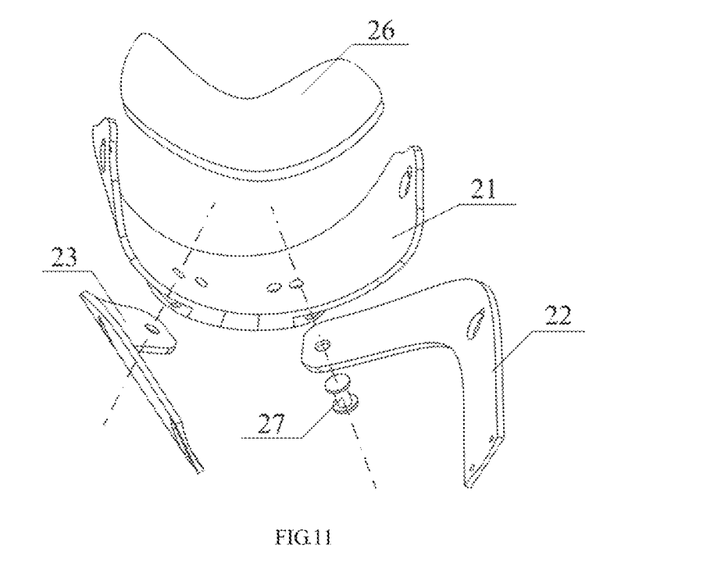
FIG. 11 shows the connection of the thigh splint and the thigh bracket of the knee protecting device shown in FIG. 3.

As shown in FIG. 11, the thigh frame 20 includes the thigh splints 22, 23, the thigh bracket 21 and a cushion pad 26. Wherein the two thigh splints 22, 23 are shaped as a curving L-shape, and the upper end portions are connected to the thigh bracket 21. A preferred connection way is hinge joint so that the thigh splint and the thigh bracket can rotate about each other. The rotation angle is within 30°, and within 10° preferably. In the present embodiment, the thigh splint and the thigh bracket are connected by screw posts. For example, a screw post 27 penetrates the through-holes on the thigh splint 22 and the thigh bracket 21 to connect the two. The thigh bracket 21 is made from flexible material, for example 65° silicon in a preferred embodiment. So the shape of the thigh bracket 21 can fit for the shape changing of the thigh in the process from bend status to straight status.

The connection points of the thigh splints 22, 23 and the thigh bracket 21 are close to the middle part of the thigh bracket 21, meanwhile the two connection points keep a distance from each other. The distance is 0~50 mm preferably, and 25 mm in the present embodiment. The cushion pad 26 is an anti-skidding cushion to enhance the bearing function of the thigh bracket 21 and prevent the knee protecting device of the present invention from sliding. It is a composite cushion with a layer of silicon drops arranged as net shape.

Figure 12:
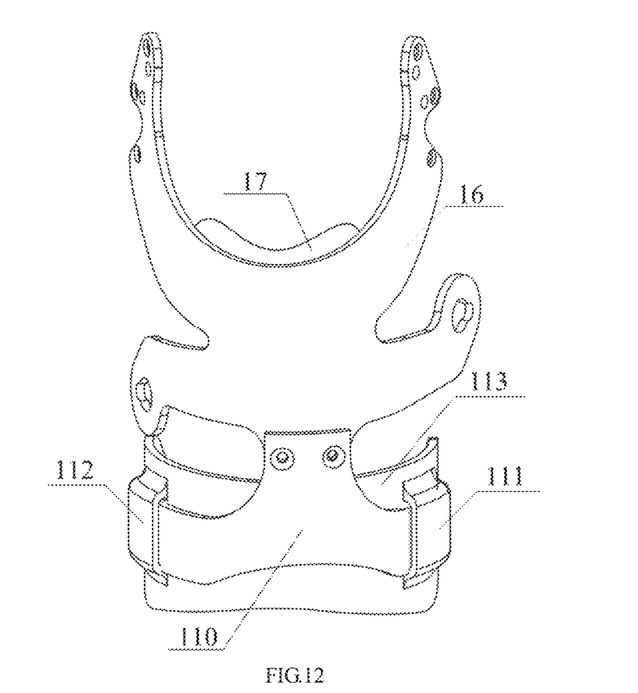
FIG. 12 shows the shank frame of the knee protecting device shown in FIG. 3.
Figure 13:
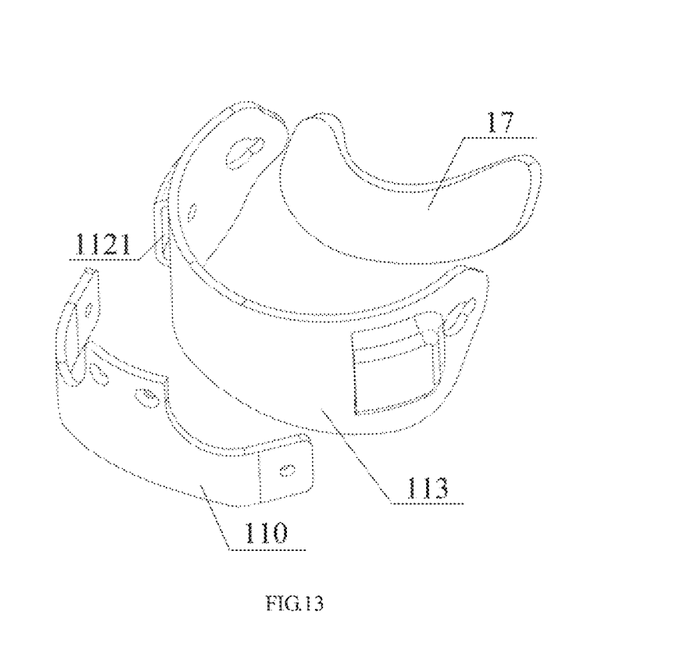
FIG. 13 is an explosive view of the shank bracket of the shank frame shown in FIG. 12.
Figure 14:
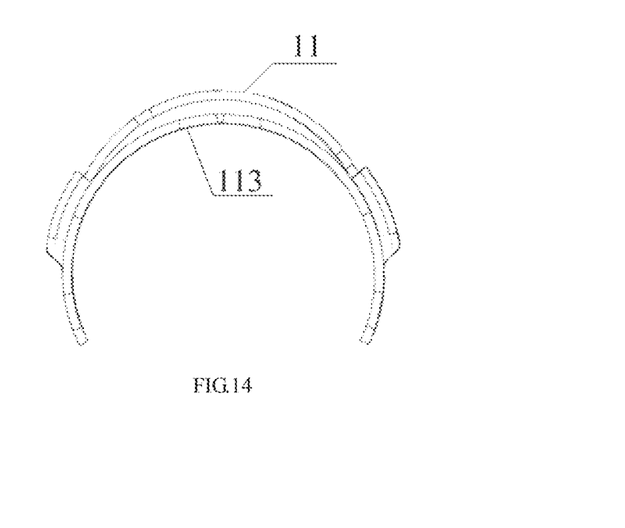
FIG. 14 shows a cross-section view of the shank bracket of the shank frame shown in FIG. 12.

As shown in FIGS. 12-13, the shank frame 10 comprises the shank splint 16, the shank bracket 11 and a cushion pad 17. Wherein the shank splint 16 is shaped like a butterfly. The two wing portions of the upper part of the shank splint 16 are connected with the groove plates of the adjustment mechanisms 31, 32 respectively, and the two wing portions of the bottom part are connected with the shank belt 14. The shank splint 16 is rigid construction. The shank bracket 11 is fixed on the shank splint 16 and placed under the shank splint 16, and the middle portions of the two are connected. The shank bracket 11 comprises a first portion 110 and a second portion 113. The first portion has a higher rigidity and is shaped as a stripe, whose middle portion is connected to the shank splint 16; the second portion 113 is a flexible and stripe-shaped piece, whereon a bulge 111 and a bulge 112 are set on both end portions. Two blind holes are formed between the bulge 111, 112 and the second portion 113, such as blind hole 1121, and are used to hold two end portions of the first portion 110. As the cross-section view shown in FIG. 14, the shank bracket 11 present a bow shape. The first portion 110 and the second portion 113 are connected at two end parts, and are separated in the middle parts. In the present embodiment, the middle interval between the two is 8 mm. The cushion pad 17 is an anti-skidding cushion to enhance the weight bearing function of the shank bracket 11 and prevent the knee protecting device of the present invention from sliding, and it is a composite cushion with a layer of silicon drops arranged as net shape in the present embodiment. The shank bracket 11 is used to fit the middle part of front surface of the shank horizontally, the shank belt 14 is used to cross over the back surface of the shank at rhombus sunk area of the posterior region of the knee, and the shank belt 15 is used to cross over the calf.

The structure and material of the thigh belts 24, 25 and the shank belts 14, 15 are the same as the description about thigh belts and shank belts in the Chinese patent A nonbearing knee orthosis (application No. CN201310347765.8), and the present invention references these descriptions. The connection way how the thigh belts 24, 25 are connected with the thigh splints 22, 23 and how the shank belts 14, 15 are connected with shank splint 16 and shank bracket 11 is the same as the description about thigh belts and shank belts in the Chinese patent A nonbearing knee orthosis (application No. CN201310347765.8), and the present invention references these descriptions. Moreover, the connection way how the thigh belts 24, 25 are connected with the thigh splints 22, 23 and how the shank belts 14, 15 are connected with shank splint 16 and shank bracket 11 can also be same as the description in the Chinese patent Fast belts of joints orthosis (application No. CN201420149171.6), and the present invention also references these descriptions.

The embodiment described above is just one preferred embodiment of the present invention. It should be known that a normal technician can create many variations without creative steps. So by logical analysis, inference and limited experiment, any art solution created based on the spirit of the present invention is in the protecting scope of the present invention.

What is claimed is:

1. A knee joint protecting device, comprising:
   a thigh frame wearable on a thigh of a lower limb of a user and a shank frame wearable on a shank of the lower limb, the thigh frame is connected to the shank frame and rotatable around a first axis to perform a first rotation, at a connection position, about the shank frame within a first position and a second position;
   wherein in the first position of the thigh frame, the knee joint protecting device is configured to fit the lower limb of the user in a standing posture; and wherein the thigh frame is configured to perform a second rotation about the shank frame, an included angle of the first axis and a rotation plane of the second rotation is within a range of 0 to 15°;
   a connection structure set between the thigh frame and the shank frame, the connection structure comprises an adjustment mechanism and a connection hinge, which are connected with each other;
   wherein the thigh frame performs the first rotation by the adjustment mechanism and performs the second rotation by the connection hinge;
   wherein the connection position is on the adjustment mechanism;
   wherein the adjustment mechanism comprises a groove plate and a sliding block, one of said groove plate and said sliding block is connected to the thigh frame by the connection hinge, and other of said groove plate and said sliding block is fixed on the shank frame;
   wherein the thigh frame is configured to stretch outwardly using the connection hinge in response to the thigh frame turning to the second position from the first position;
   and wherein the thigh frame is configured to shrink inwardly using the connection hinge in response to the thigh frame turning to the first position from the second position;
   wherein the connection hinge comprises a first hinge part and a second hinge part, which rotate about each other on a first rotation plane;
   wherein the second hinge part is rotatably connected to the adjustment mechanism, the second hinge part and the adjustment mechanism rotate about each other on a second rotation plane; and
   wherein in the first position of the thigh frame, an included angle of the first rotation plane and the second rotation plane is 90°±40°.

2. The knee joint protecting device according to claim 1, further comprising two said connection structures; wherein the thigh frame comprises two thigh splints configured to fit the user's thigh, the connection hinges of the two connection structures are respectively connected with the two thigh splints; wherein each connection hinge comprises the first hinge part and the second hinge part, which rotate about each other, the first hinge part is fixed on the thigh frame, the second hinge part is rotatably connected to the adjustment mechanism; and wherein in the first position of the thigh frame, an included angle of the first axis and a rotation axis of the respective first hinge parts of the two connection hinges in the first position of the thigh frame is 90°±30°.

3. The knee joint protecting device according to claim 2, wherein the shank frame comprises a shank bracket configured to fit a middle part of the user's shank horizontally, the shank bracket comprises a first portion and a second portion with a different curvature, two end portions of the first portion of the shank bracket and two end portions of the second portion of the shank bracket are respectively connected to each other, the first portion is less flexible than the second portion, and the first portion is set at outside of the second portion.

4. The knee joint protecting device according to claim 3, wherein the shank frame further comprises a shank splint, shaped like a butterfly, configured to fit a top part of the user's shank; the shank splint comprises a middle portion and four wing portions extending from the middle portion; two of said four wing portions extend obliquely upward from an upper part of the middle portion and two ends of said two of said four wing portions are connected to two said adjustment mechanisms, respectively; two remaining of said four wing portions extend horizontally from a lower part of the middle portion and two ends of said two remaining of said four wing portions are connected with two ends of a first shank belt, respectively; the first shank belt is configured to cross over a back surface of the user's shank at a rhombus sunk area of a posterior region of the user's knee; and wherein the middle portion of the shank splint is connected to the first portion of the shank bracket.

5. The knee joint protecting device according to claim 4, wherein two ends of the second portion of the shank bracket are connected with two ends of a second shank belt, respectively, the second shank belt is configured to cross over the user's calf.

6. The knee joint protecting device according to claim 3, wherein the end portions of the first portion and the second portion of the shank bracket are connected by screw posts.

7. The knee joint protecting device according to claim 4, further comprising a cushion pad set on an inner surface of the second portion of the shank bracket, a surface of the cushion pad is a layer of net-shaped silicon.

8. The knee joint protecting device according to claim 2, wherein each second hinge part is fixed onto its respective adjustment mechanism.

9. The knee joint protecting device according to claim 8, wherein said each second hinge part is connected to its respective adjustment mechanism by a rivet or a screw.

10. The knee joint protecting device according to claim 2, wherein each second hinge part is rotatably connected to its respective adjustment mechanism; and said each second hinge part and its respective adjustment mechanism rotate about each other on the second rotation plane.

11. The knee joint protecting device according to claim 10, wherein said each second hinge part is connected to its respective adjustment mechanism by a hinge pin, and a relative rotation of said each second hinge part and its respective adjustment mechanism is performed around the hinge pin.

12. The knee joint protecting device according to claim 2, wherein one of the two thigh splints is a first thigh splint configured to fit on an inner side of the user's thigh and the other thigh splint is a second thigh splint configured to fit on an outer side of the user's thigh, the two connection structures are configured to fit on two sides of the knee joint, respectively.

13. The knee joint protecting device according to claim 1, further comprising two said connection structures; wherein the thigh frame comprises two thigh splints configured to fit the user's thigh; wherein each connection hinge comprises the first hinge part and the second hinge part, the first hinge parts of the connection hinges of the two connection structures are fixed on the thigh frame, respectively; and wherein in the first position of the thigh frame, an included angle of the first axis and a rotation axis, around which the first hinge part rotates about the second hinge part, is 90°±30°.

14. The knee joint protecting device according to claim 13, wherein one of the two thigh splints is a first thigh splint configured to fit on an inner side of the user's thigh and the other thigh splint is a second thigh splint configured to fit on an outer side of the user's thigh, the two connection structures are configured to fit on two sides of the knee joint, respectively.

15. The knee joint protecting device according to claim 14, wherein said each second hinge part is connected to its respective adjustment mechanism by a hinge pin, and a relative rotation of said each second hinge part and its respective adjustment mechanism is performed around the hinge pin.

16. The knee joint protecting device according to claim 1, wherein the thigh frame further comprises two thigh splints configured to fit the user's thigh and a thigh bracket configured to horizontally fit a front surface of the user's thigh; wherein end portions of the two thigh splints, which are away from shank splints of the shank frame, are connected to the thigh bracket, the thigh bracket is a flexible construction with a curving shape; and wherein a curve radius of the thigh bracket is configured to decrease in response to the thigh frame shrinking inwardly and is configured to increase in response to the thigh frame stretching outwardly.

17. The knee joint protecting device according to claim 16, wherein each thigh splint is rotatable around its respective connecting point where said each thigh splint connects to the thigh bracket.

18. The knee joint protecting device according to claim 17, further comprising a cushion pad set on an inner surface of the thigh bracket, a surface of the cushion pad is a layer of net-shaped silicon.

* * * * *